United States Patent
Ishiguro et al.

[11] Patent Number: 5,898,491
[45] Date of Patent: Apr. 27, 1999

[54] SURFACE DEFECT TEST METHOD AND SURFACE DEFECT TESTER

[75] Inventors: Takayuki Ishiguro; Izuo Horai; Kazuya Tsukada, all of Kanagawa-ken, Japan

[73] Assignee: Hitachi Electronics Engineering Co. Ltd., Tokyo, Japan

[21] Appl. No.: 09/049,015

[22] Filed: Mar. 27, 1998

[30] Foreign Application Priority Data

Mar. 28, 1997 [JP] Japan ...................................... 9-095037

[51] Int. Cl.$^6$ .................................................. G01N 21/88
[52] U.S. Cl. ...................................... 356/243.4; 356/237.2
[58] Field of Search ............................ 356/243.1, 243.4, 356/243.6, 237.2, 237.3

[56] References Cited

U.S. PATENT DOCUMENTS

| | | | |
|---|---|---|---|
| 4,636,073 | 1/1987 | Williams | 356/243.4 |
| 5,004,340 | 4/1991 | Tullis et al. | 356/243.6 |
| 5,214,486 | 5/1993 | DeWitt | 356/243.6 |
| 5,258,974 | 11/1993 | Ishimura et al. | 356/243.4 |

*Primary Examiner*—Richard A. Rosenberger
*Attorney, Agent, or Firm*—Fay, Sharpe, Beall, Fagan, Minnich & McKee

[57] ABSTRACT

The surface defect test method and tester according to the invention comprises a sensitivity calibration disk formed with n (n is an integer equal to or larger than 2) false defect rows each including 3 or more false defects each formed in a radial or peripheral direction provided in the peripheral direction of the calibration disk at a predetermined angle pitch. The false defects of each false defect row take in the form of protrusions or recesses having substantially the same size, adjacent ones of the false defects are physically separated by a predetermined distance larger than a width of a laser spot and the false defects of a certain one of the false defect rows are different in size from the false defects of other false defect rows, regulating the detection sensitivity according to a result of the test, producing, from a result of a test of the calibration disk with the regulated detection sensitivity, data relating a level of a detection signal to a size of the false defect as a reference data for determination of the size and obtaining the size of the defect from the level of the detection signal when the disk to be tested on defect on the basis of the reference data for determination of the size.

15 Claims, 7 Drawing Sheets

| OUTPUT SIGNAL LEVEL | DEFECT SIZE | FLAG |
|---|---|---|
| 101.7 | A | |
| 121.8 | B | |
| 133.5 | C | |
| 145.6 | D | |
| ⋮ | ⋮ | |

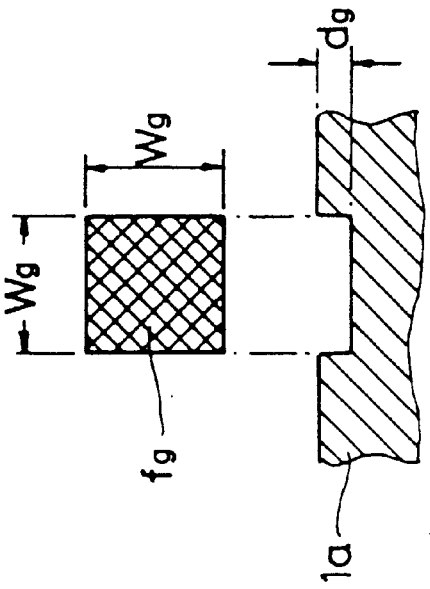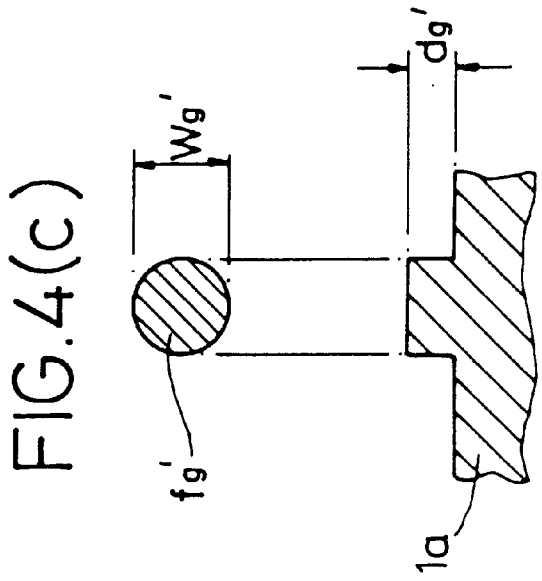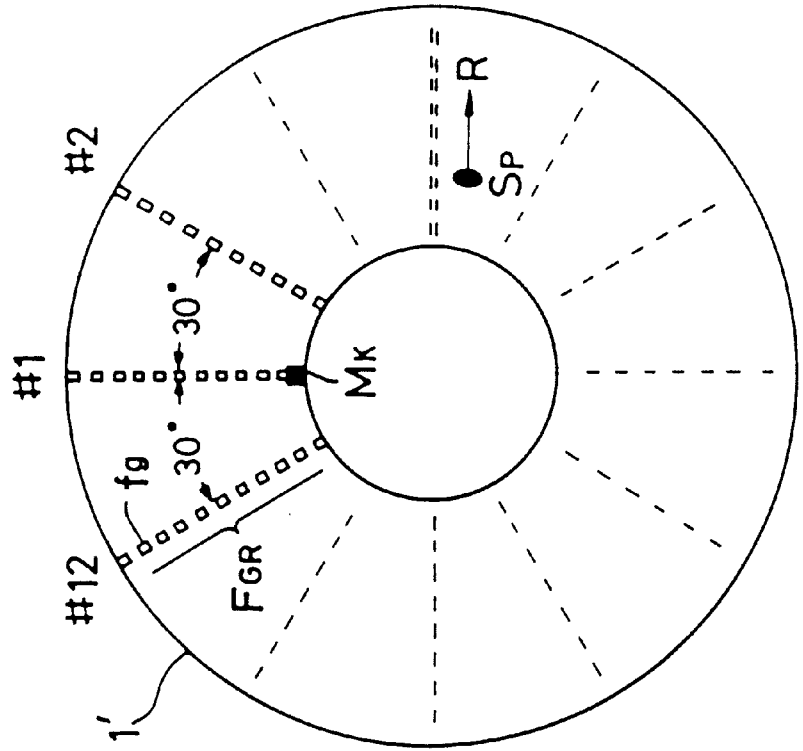

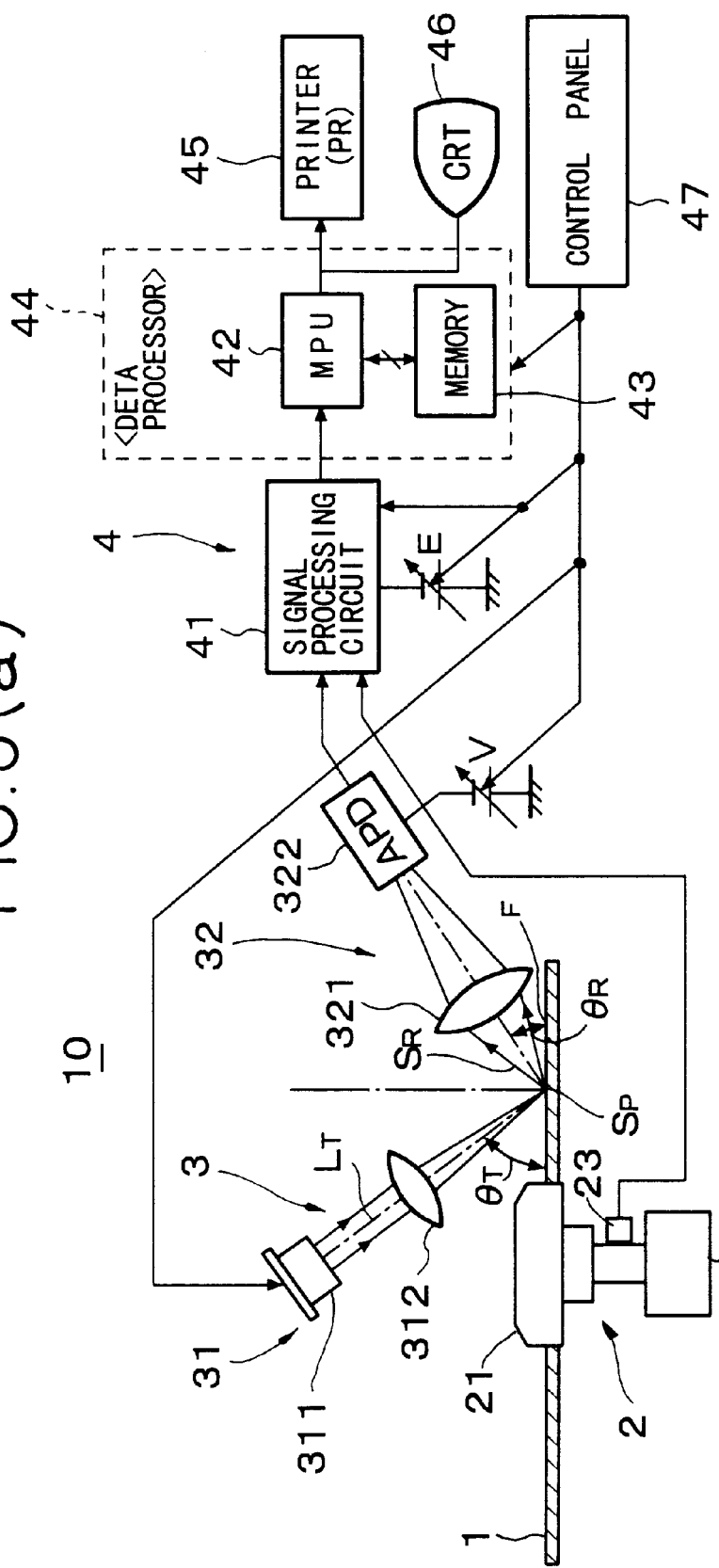
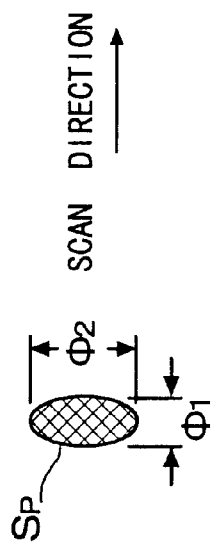
FIG.8(a)
FIG.8(b)

SURFACE DEFECT TEST METHOD AND SURFACE DEFECT TESTER

DESCRIPTION

1. Technical Field

The present invention relates to a defect test method and a defect tester and, particularly, to a surface defect test method for detecting surface defects on a magnetic disk and a surface defect tester, which can improve the preciseness of size classification of defect and restrict a variation of data of a test result.

2. Background Art

A semiconductor wafer or a hard magnetic disk used as a recording medium of a computer system is tested on surface defect and size thereof in some of the fabrication steps thereof. That is, the test on the surface defect of a disk is performed in various fabrication steps, for example, in a state of a polished disk substrate, in a state of a disk plated with a metal and in a state of a magnetic disk having a magnetic thin film thereon obtained by painting the metal plated disk with a magnetic material, etc.

FIG. 8(a) shows a main portion of a surface defect tester for detecting surface defects of a magnetic disk.

In FIG. 8(a), the surface defect tester 10 is constructed with a rotary mechanism 2, an optical detection system 3 and a defect detector 4. A disk 1 to be tested is mounted on a spindle 21 of the rotary mechanism 2 and rotated by a motor (M) 22. The optical detection system 3 is constructed with a light projection system 31 including a laser light source 311 and a condenser lens 312 and a optical light receiving system 32 including a condenser lens 321 and a light receiver 322. A laser beam LT produced by the laser light source 311 is condensed by the condenser lens 312 to a laser spot Sp on a surface of the disk 1.

By moving the spot Sp in a radial direction R of the disk 1 while rotating the disk 1, the laser spot Sp scans the surface of the disk 1 coaxially or spirally. In this case, in order to make a total scan time of the disk 1 as short as possible, an area of the laser spot Sp is made ellipsoidal having a length $\phi 1$ in a minor axis direction and a length $\phi 2$ in a major axis direction as shown in FIG. 8(b). The major axis is arranged in the radial direction of the disk to increase a scan width of the laser spot in the radial direction.

The laser spot Sp is scattered by a defect F on the surface of the disk 1. A scattered light SR is condensed by the condenser lens 321 of the optical light receiving system 32 and the condensed scattered light is received by the light receiver 322 composed of an opto-electric conversion element such as an avalanche photo-diode (APD) or a photo-multiplier tube (PMT). An output of the light receiver 322 is input to a signal processing circuit 41 of the defect detector 4 and the defect F is detected by a defect detection signal output from the signal processing circuit 41. The size of the defect F is detected according to an amplitude of the output signal of the light receiver 322, that is, the detection signal.

The signal processing circuit 41 includes an amplifier for amplifying the output signal of the light receiver 322, a sampling circuit for sampling the amplified output signal corresponding to a defect which is larger than noise component of the output signal with a pulse supplied from a rotary encoder 23 and storing a peak value of the sampled output signal as a level value of the detection signal of the defect as a detected defect value, an A/D converter for digitizing the sampled peak value and a position data producing circuit responsive to the pulse from the rotary encoder 23 for producing a position data on the disk, etc.

The signal processing circuit 41 simultaneously sets a plurality of different threshold values for the output signal output from the light receiver 322 and detects the size of defect according to the level of the output signal which exceeds any one of the threshold values. In this case, when the threshold values are set in stepwise finely, the size of defect corresponds to the output signal value and, when the threshold values are relatively roughly set, defects having various sizes are detected as those fallen in a certain class. The detection value is output as a digital value and the position data producing circuit produces data of the detection value indicative of the defect size or the classified defect size and position data thereof.

The digital size data of the respective defects, that is, the data of detected defect value, and the digital position data thereof on the disk are supplied from the signal processing circuit 41 to a data processor 44. The data processor 44 is composed of a MPU 42 and a memory 43, etc. The number of defects of each size are counted in the data processor 44 and the size data and the count value of the defects, etc., are output to a printer (PR) 45 together with the position data of the defects on the disk 1. In this case, these data may be printed out as a map on the disk. Further, the position data is displayed on a screen of a display (CRT) 46, etc., as a map on the disk. The count value of the defects in each class of size is also displayed on the screen separately. When the data processor 44 receives the detected defect value from the signal processing circuit 41, a classification processing produces the size data of defect by classifying the detected defect value according to the size of defect internally. It should be noted that the term "size" used in this specification means a size of defect in plan view and a depth or height thereof.

The defect F on the disk 1 may have various sizes and an example thereof is shown in FIG. 9.

In FIG. 9, a defect Fh takes in the form of a shallow pit or saucer pit and has a relatively large diameter Dh and has a depth dh smaller than the diameter Dh. A defect Fp takes in the form of a deep well having a relatively small diameter Dp and a large depth dp and is usually called as merely a pit. The defects Fh and Fp usually exist discretely. A defect Fs takes in the form of a groove and is called as scratch defect. Such scratch defect may have various width ws and depth ds. There may be other defects having other shapes and sizes than those mentioned above. Further, there may be defects called extraneous substances having various sizes. Such extraneous substance may be fine particles attached onto the surface of the disk 1.

In order to detect defects having various shapes and sizes, the defect tester 10 regulates the detection sensitivity for defects by appropriately setting parameters related to the level of detection signal, such as a projection angle $\theta T$ of the laser beam LT of the optical projection system 31, a light receiving angle $\theta R$ of the light receiving system 32, a voltage V applied to the light receiving element, that is, the avalanche photo diode APD, a gain of the amplifier provided within the signal processing circuit 41, a threshold voltage E for removing noise and the laser output of the laser light source 311, etc., through the control panel 47 including the control circuit.

As mentioned previously, the size of defect is determined by not only the area but also the depth or the height (volume).

The defect detection sensitivity of the surface defect tester 10 is optimally set for each of various defects F. However, the regulation of sensitivity requires skills. Particularly, it is very difficult to regulate the sensitivity such that the tester can detect shallow defect to deep defect or can detect small extraneous substance to large extraneous substance. Further, it is impossible to obtain defect data by which the size of defect can be correctly classified, unless the regulation of defect detection sensitivity is calibrated according to a constant reference. Further, defect detection data of various sizes of defects or various classified sizes of defects vary under influence of setting conditions of the tester. Further, there is a tendency that a variation of defect detection data occurs between different testers, causing a common use of the defect detection data to be difficult.

The calibration of the detection sensitivity of the conventional tester is performed by using disks which have shallow pit, pit and scratch which have known sizes corresponding to defects to be detected and sizes thereof as sample defects or disk which have extraneous substances having specific heights, as sample disks and detecting the defects of the respective sample disks. However, since the defects of the respective sample disks have specific shapes of specific sizes, there may be cases where the detection sensitivity calibrated thereby becomes not appropriate in view of a range of classified size of defects to be detected and there may be deviation of the detected size or the classification. Further, it is practically impossible to known the preciseness of the classification of defect size in the surface defect test.

With the recent increase of recording density of a disk, the range of size of defect to be detected is reduced or there is a tendency that the defect detection is directed to a smaller size. However, it is very difficult to obtain sample disks for detection sensitivity calibration which are appropriate for the classification of sizes.

SUMMARY OF THE INVENTION

An object of the present invention is to provide a surface defect test method which can improve the preciseness of size classification of defect and restrict a variation of data of a test result.

Another object of the present invention is to provide a surface defect tester which can improve the preciseness of size classification of defect and restrict a variation of data of a test result.

In order to achieve the above objects, a surface defect test method according to the present invention is featured by comprising the steps of testing a sensitivity calibration disk formed with n (n is an integer equal to or larger than 2) false defect rows each including 3 or more false defects arranged radially or peripherally of the calibration disk with a predetermined angular space, the false defects of each false defect row taking in the form of protrusions or recesses having substantially the same size, adjacent ones of the false defects of each false defect row being physically separated from each other by a predetermined distance larger than a width of a laser spot and the false defects of a certain one of the false defect rows being different in size from the false defects of other false defect rows, regulating the detection sensitivity according to a result of the test, producing, from a result of a test of the calibration disk with the regulated detection sensitivity, data relating a level of a detection signal to a size of the false defect as a reference data for determination of the size and obtaining the size of the defect from the level of the detection signal when the disk to be tested on defect on the basis of the reference data for determination of the sizes.

The surface defect tester according to the present invention is featured by comprising the sensitivity calibration disk mentioned above, sensitivity regulation means for regulating the detection sensitivity, reference data producing means for producing, from a result of a test of the calibration disk with the regulated detection sensitivity, data relating a level of a detection signal to a size of the false defect as a reference data for determination of the size and size detection means for obtaining the size of the defect from the level of the detection signal when the disk to be tested is tested on defect on the basis of the reference data for determination of the size.

When an operator performs a defect test by using a surface defect tester with using the above mentioned sensitivity calibration disk as an object to be tested on surface defect and displays a result of test, that is, detection values of the size of defects detected correspondingly to levels of detection signals or a classified value of the defect size classified according to the level of the detection signal thereof, on a display device, the defects are displayed together with an image of the disk on the display device as a map. In this case, since at least an image corresponding to false defects having different sizes is obtained, it is possible to regulate the sensitivity of the surface defect tester such that an image corresponding to an appropriate detection sensitivity is obtained, while watching the thus obtained image on the display device.

Therefore, it is possible without skills to appropriately regulate the detection sensitivity for the size classification of defect while watching the image of the calibration disk on the display device. Further, since it is possible to reproduce the setting condition of the defect detection sensitivity of the surface defect tester so long as the same calibration disk is used, a test result data is hardly influenced by the setting condition and a variation of data is reduced. Of course, such variation of detection result data hardly occurs even between different surface defect testers and a common use of the data becomes possible between different surface defect testers.

Therefore, it is possible to appropriately regulate the detection sensitivity correspondingly to the size classification of the defect to be detected, while watching the image of the false defect displayed on the display screen. Particularly, it is possible to regulate the detection sensitivity of the surface defect tester for a defect whose size is substantially an intermediate of the size classification. In such case, it is possible to know sizes which can fall within a class correspondingly to the sensitivity regulation from the displayed condition of the false defects on the display screen.

The detected defect value (level of the detection signal) corresponding to the size of the false defect under the appropriately regulated sensitivity is obtained from the result of the test and the data relating the detected defect value to the size of the false defect is produced as the reference data for size determination. By determining the defect size on the basis of the reference data, data indicative of the defect size detected in the disk defect tester or the classified size data is substantially correctly calibrated.

By performing the calibration of detection sensitivity to the surface defect tester at every start time of test or similarly applying the calibration to a number of other surface defect testers, a variation of detection sensitivity and/or test result data which may occur in every test or a variation of detection sensitivity or test result data which may occur between the testers can be restricted.

As a stepwise selection range of size of the respective false defects of a false defect row, which may take in the form of protrusions or recesses, it is preferable that a length of one side thereof is within a range from 0.5 µm to 20 µm and a depth or height in a range from 0.01 µm to 0.75 µm when the shape of the false defect is square or rectangular When the shape of the false defect is circular, it is preferable that a diameter is within a range from 0.5 µm to 20 µm and a depth or height is within a range from 0.01 µm to 0.75 µm.

BRIEF DESCRIPTION OF THE DRAWINGS

FIG. 4 shows a concrete example of a sensitivity calibration disk used in the present invention, in which FIG. 4(a) shows an arrangement of false defect rows of the sensitivity calibration disk, FIG. 4(b) illustrates square recesses formed in the false defect row and FIG. 4(c) illustrates circular protrusions formed in the false defect row;

FIG. 8 shows schematically a construction of a main portion of the magnetic disk defect tester, in which FIG. 8(a) shows a whole construction thereof and FIG. 8(b) a laser spot thereof.

DESCRIPTION OF THE PREFERRED EMBODIMENTS

Figure 1:
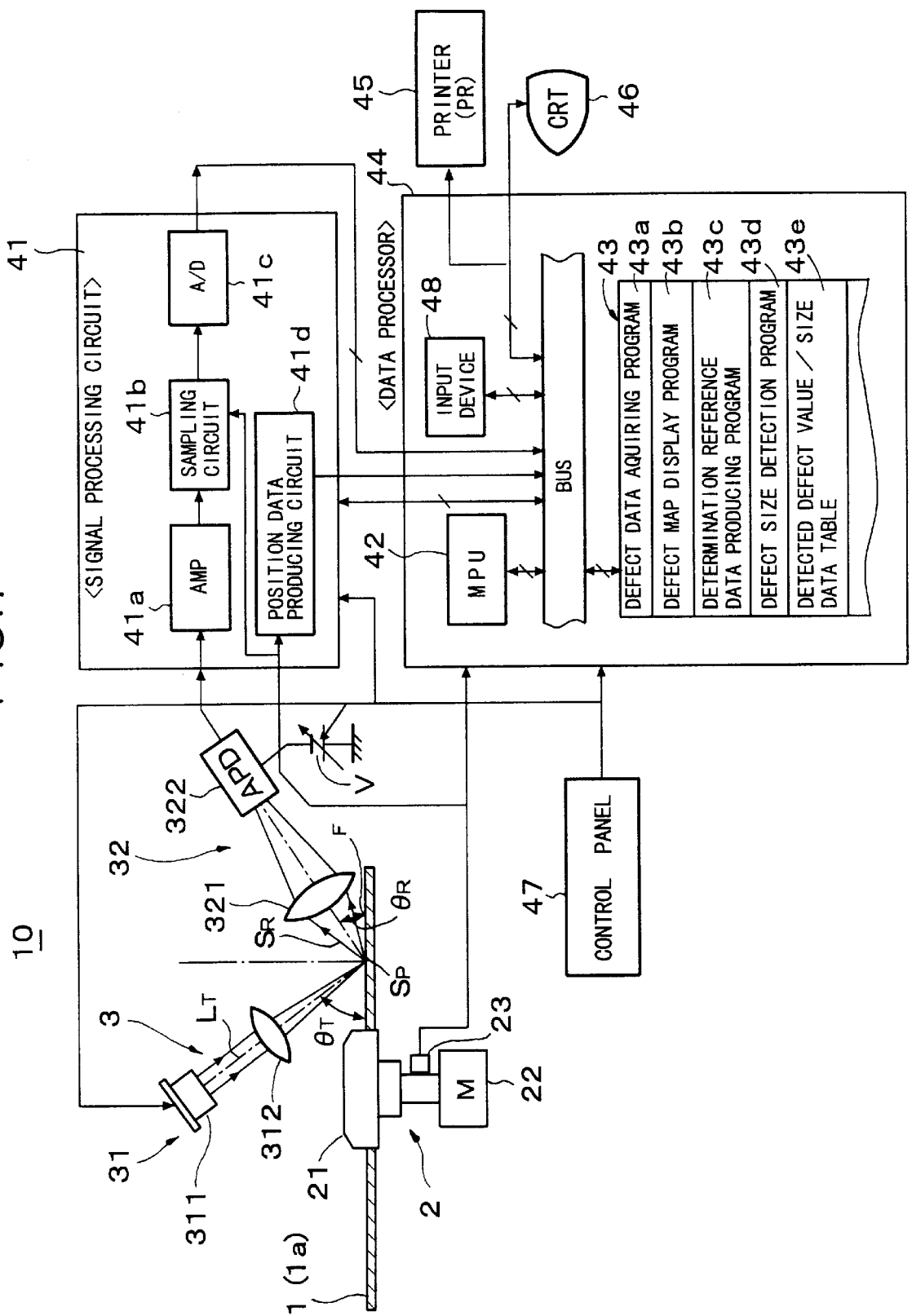
FIG. 1 is a block diagram showing an embodiment of a magnetic disk defect tester which uses the surface defect test method to which the present invention is applied.

A magnetic disk defect tester 11 shown in FIG. 1 includes a data processor 50 in lieu of the data processor 44 shown in FIG. 8. The data processor 50 includes an input unit 48 in addition to the data processor 44, the MPU 42 and the memory 43 shown in FIG. 8. Further, the memory 43 of the data processor 50 stores a defect data pick-up program 43a, a defect map display program 43b, a determination reference data producing program 43c, a defect size detection program 43d and a detected defect value/defect size table 43e, etc.

Figure 6:
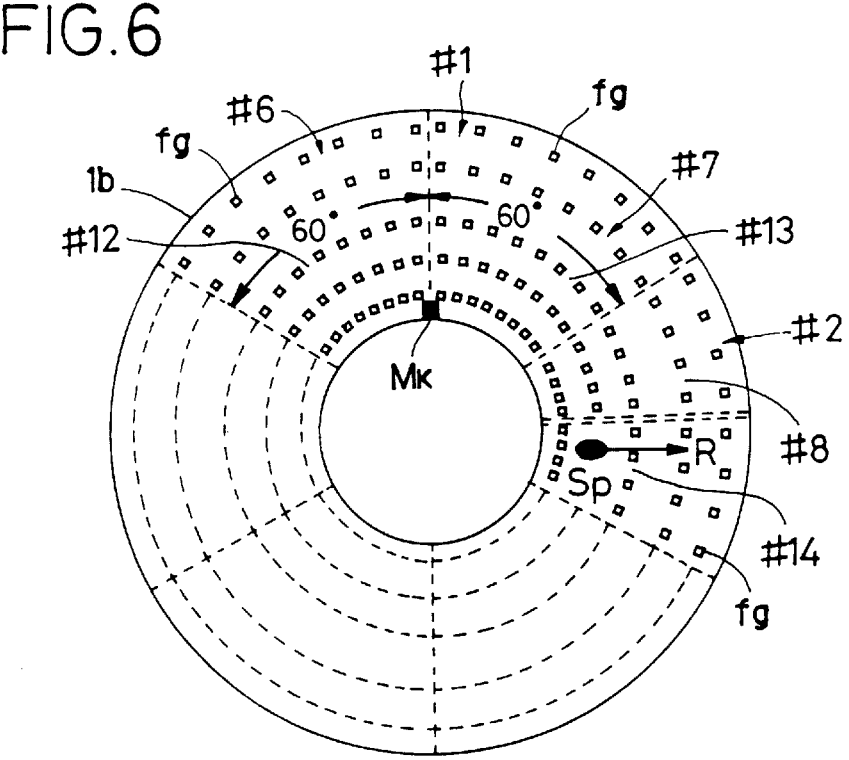
FIG. 6 shows a sensitivity calibration disk according to another embodiment of the present invention.

During a calibration of the detection sensitivity, the data processor 50 tests on surface defect a sensitivity calibration disk 1a (1b) having false defect rows having false defects of various sizes shown in FIGS. 4 and 6 and produces the detected defect value/defect size table 43e on the basis of a result of the test. Then, when a defect test is performed for a disk to be tested, the defect is classified in size by converting the level of the detection signal obtained by the defect test into data indicative of the defect size or the classified size with reference to the detected defect value/ defect size table 43e.

The signal processing circuit 41 produces the detected defect value by detecting the defect described with reference to the previously mentioned prior art. The signal processing circuit 41 comprises an amplifier 41a for amplifying an output signal of the light receiving element 322, a sampling circuit 41b for obtaining a detection value by sampling peak values of the output signal amplified by the amplifier 41a which exceed noise component thereof in accordance with a pulse from the rotary encoder 23, an A/D converter (A/D) 41c for digitizing the sampled detection value and a position data producing circuit 41d for producing a position data on the disk in response to the pulse from the rotary encoder 23, etc.

The MPU 42 of the data processor 50 executes the defect data aquiring program 43a to spirally scan the disk 1 with a laser spot Sp and stores an A/D converted value of the detected defect value and the position data sequentially received from the signal processing circuit 41 in a work area of the memory 43 or a buffer memory portion correspondingly to the scanning. When the scanning of the whole surface of the disk 1 is completed, the MPU 42 calls the defect map display program 43b and executes the latter during the detection sensitivity calibration. During the defect test of a usual disk, it calls the defect size detection program 43d and executes the latter.

When the defect size detection program 43d is executed by the MPU 42, respective tracks of the disk 1 to be tested are sequentially scanned to test the disk on surface defect. The detected defect value obtained by this defect test is classified by converting it into data of the size of defect by referencing to the detected defect value/defect size table 43e and results of classification are stored sequentially in the memory 43 together with the position data of the defects. When the scanning of the whole surface of the disk 1 is completed, the MPU 42 counts defects of every defect size and stores the count in the memory 43. Thereafter, the MPU 42 calls and executes the defect map display program 43b to display the classified test result as a map and outputs it to a printer 45, etc. During the calibration of detection sensitivity, the defect size detection program 43d is executed to set data by reading in a size conversion data with which data of defect size corresponding to the defect detection value (level of the detection signal) or data of classified size value obtained by further finely classifying the defect size is produced in the detected defect value/defect size table 43e and rewriting it. The rewritten conversion data is preliminarily obtained experimentally or empirically. In the defect test during the detection sensitivity calibration, a result of the defect test is displayed on the display device 46 by the detected defect value/defect size table 43e having such conversion data in the form similar to an actual state of defect.

When the defect map display program 43d is executed by the MPU 42, the position data of the defect and the defect size data are read out. The defect size data is converted into a pattern data having a size corresponding to the defect size data to produce a display data and display it on the display 46 as a map by extending the pattern data to an image data displaying it in a predetermined coordinates indicated by the position data.

The determination reference data producing program 43c is a program for rewriting a content of the detected defect value/defect size table 43e and, when it is executed by the MPU 42, a display coordinates position is detected from a position of the map display on the screen assigned by a mouse, etc., when the defect size is input from the input device 48. The size data of the defect displayed in the display coordinates position or a position closest to the display coordinates position is extracted from the result of the test. Further, on the basis of the extracted data, the corresponding size data in the detected defect value/size data table 43e is searched and the searched size data is updated to the input size data. Further, a flag indicative of the update is written correspondingly to the updated size data. In this manner, the size data of the detected defect value/defect size table 43e is updated to the input size data. At a time when the update is completed, the detected defect value/defect size table 43e is produced by erasing the past data having no flag. Thus, the detected defect value/defect size table 43e having new determination reference data whose relation between the detection signal and the size is calibrated is produced.

In this case, it is possible to separately produce another table by extracting the detected defect value corresponding to the size data from the detected defect value/defect size table 43e and producing a conversion data pairing the detected defect value and the input defect size. The conversion data is updated by producing a plurality of pairs of the detected defect values and the defect sizes and writing the content of the thus produced new table in the detected defect value/defect size table 43e.

Incidentally, such rewriting of the size data of the detected defect value/defect size table 43e is performed at a time of the detection sensitivity calibration, that is, when the defect test of the sensitivity calibration disk 1a (1b) is performed.

Figure 3:
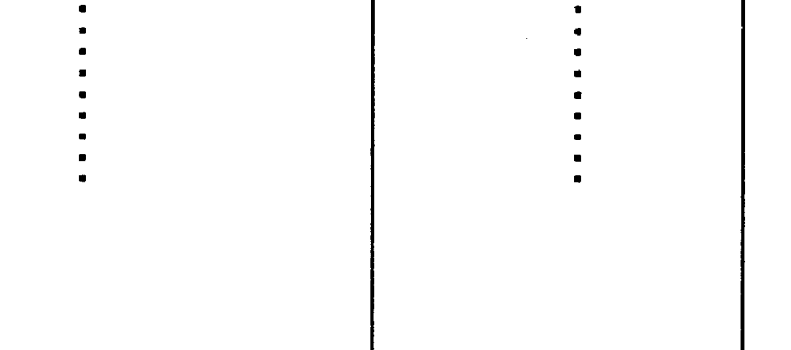
FIG. 3 is a detected defect value/defect size table.

The construction of the detected defect value/defect size table 43e is a contrast table corresponding the signal level to the defect size and including a column of flags indicative of updated data, as shown in FIG. 3. This table stores standard data of the signal level and the defect size initially and can be rewritten. Therefore, it can be constructed with a memory such as EEPROM which can be rewritten or a RAM, and the conversion data is updated by reading in data from an external memory device such as hard disk or flexible disk.

A sensitivity calibration disk (referred to as "reference disk", hereinafter) 1a shown in FIG. 4(a) is a disk made from an aluminum disk having mirror polished surfaces. The aluminum disk is put in a target position of an ion beam sputtering device and a desired false defect in the form of a recess is formed by sputtering a position of the aluminum disk corresponding thereto with ion beam. By forming a number of pits in a specific row in this manner, a row of false defects are formed. Such false defect may be formed by melting a portion of the disk surface by laser beam. In the latter case, the false defect may be a circular pit. Alternatively, false defects in the form of recesses can be formed by etching with using a resist as a mask.

On the other hand, false defects in the form of protrusions may be formed by adhering particles sputtered from the target by an ion beam sputtering device to the aluminum disk through a mask having a plurality of holes. In this case, a metal material of the target is preferably tungsten. The false defects in the form of protrusions may be selectively formed along a radial direction or peripheral direction of the aluminum disk by epitaxially growing aluminum by VCD through a photo resist.

As shown in FIG. 4(a), for example, 12 false defect rows #1, #2, . . . , #12 each including a number of false defects fg in the form of recesses may be formed along equiangularly spaced 12 radial directions by the ion beam sputtering device. The false defects fg take in the form of square recesses having the same size. The size of the false defect fg is controlled by controlling the amount of ion beam, the mass of particle used, the time of ion beam bombardment and the sputtering position, etc. Cross sectional diameter of ion beam used in this case is about one fourth to one tenth of a length of one side of a square false defect. A plurality of positions along one of the lateral sides of the square recess to be formed are bombarded with ion beam and the bombardment is repeated while in stepwise shifting the ion beam vertically. For example, in a case where a false defect in the form of a square recess having one side length wg of 1 $\mu$m, at least 5 points along one lateral side of the false defect to be formed are bombarded with ion beam having a cross sectional diameter of, for example, 0.2 $\mu$m. Then, the ion beam is shifted vertically by 0.2 $\mu$m and 5 points along a direction parallel with the lateral direction are bombarded with the same beam. This procedure is repeated through 4 vertical shifts of the ion beam and the total of 25 ion beam bombardments result in the false defect fg in the form of the square recess having one side length of 1 $\mu$m as shown in FIG. 4(b). This processing is repeated a plurality of times corresponding to the number of false defects along each of the 12 radial directions of the disk 1a to form the false defects with a pitch larger than a radial width (major axis length) $\phi 2$ of the laser spot Sp. A position of the false defect to be formed next in the peripheral direction which is the scan direction of the laser spot Sp is, of course, remote from a preceding false defect by a distance much larger than the peripheral width (minor axis length) $\phi 1$ of the laser spot Sp.

A mark Mk provided on an inner periphery of the false defect row indicates that false defect row is a reference false defect row #1. The mark Mk is provided as a false defect having a shape desired as a mark having a size larger than the other false defects. In this embodiment, the respective false defect rows are formed such that the size of false defects of the rows which are on a certain radial position increases with positions thereof along a clockwise direction, so that a group FGR of the false defects fg having different size can be identified. Incidentally, it should be noted that the increase of the defect size along the clockwise direction means a reduction of the defect size in the counterclockwise direction. Therefore, the increase and reduction are a relative matter.

Although, in FIG. 4(a), the false defects of only the false defect rows #1, #2 and #12, which take in the form of the square recesses are shown, it should be noted that the side widths Wg and the depths dg (FIG. 4(b)) of the false defects are increased in stepwise from the false defect row #1 to the false defect row #12. However, since differences in side width and in depth between the false defects of adjacent false defect rows are so small that it is very difficult to illustrate such differences clearly, the size of the false defects including the depth thereof is shown as substantially the same in FIG. 4(a).

The ranges of the side length wg and the depth dg of the false defect fg shown in FIG. 4(b) may be as follows although other ranges may be used:

Size of False Defect fg wg: 0.5 $\mu$m, 1 $\mu$m, 3 $\mu$m, 5 $\mu$m, 10 $\mu$m, 20 $\mu$m dg: 0.025 $\mu$m, 0.05 $\mu$m, 0.02 $\mu$m, 0.75 $\mu$m The ranges of the side length wg and the depth dg mentioned above are enough to cover the side length and depth of the practical defect size.

In a case where the size of defects is classified with using the defect side length of, for example, 1 $\mu$m as a center or reference, wg=1 $\mu$m, wg=0.5 $\mu$m and wg=3 $\mu$m are selected as the side lengths of false defects and used in such combinations as follows:

The side length wg of the false defects of the false defect row #1 is made 0.5 $\mu$m and the depth thereof is made 0.025 $\mu$m, those of the false defect row #2 are made 0.5 $\mu$m and 0.025 $\mu$m, respectively, the false defects of the false defect row #3 are made 0.5 $\mu$m and 0.02 $\mu$m, respectively, those of the false defect row #4 are made 0.5 $\mu$m and 0.025 $\mu$m, respectively, the false defects of the false defect row #5 are made 1 $\mu$m and 0.025 $\mu$m, respectively, those of the false defect row #6 are made 1 μm and 0.05 μm, respectively, the false defects of the false defect row #7 are made 1 μm and 0.2 μm, respectively, those of the false defect row #8 are made 1 μm and 0.75 μm, respectively, those of the false defect row #9 are made 3 μm and 0.025 μm, respectively, those of the false defects of the false defect row #10 are made 3 μm and 0.05 μm, respectively, those of the false defect row #11 are made 3 μm and 0.2 μm, respectively, and the false defects of the false defect row #12 are made 3 μm and 0.75 μm, respectively. The increase in depth of false defects of the respective false defect rows are 0.025×2, 0.025×4, 0.025×20 and 0.025×30 with 0.025 μm as a reference value.

The 12 false defect rows each having the false defects fg different in size from the other false defect rows are shown in FIG. 4(a). In FIG. 4(a), the size of the false defects in one row in an upstream in the clockwise direction is smaller in stepwise than that in a downstream in the clockwise direction.

In a case where the center size of defects to be classified is, for example, 5 μm, the reference disk 1a having 12 false defect rows including false defects whose one side sizes are 3 μm, 5 μm and 10 μm for respective depths is prepared.

Where the angular pitch of the false defect rows is 15°, it is possible to provide a reference disk having 24 false defect rows. Thus, the single reference disk can include both of the above mentioned two examples each including 12 false defect rows. That is, the false defect rows including false defects fg whose sizes are gradually increased every row are provided for each of the combinations of the above mentioned wg0.5 μm, wg=1 μm, wg=3 μm, wg=5 μm, wg=10 μm and wg=20 μm.

Figure 5A:
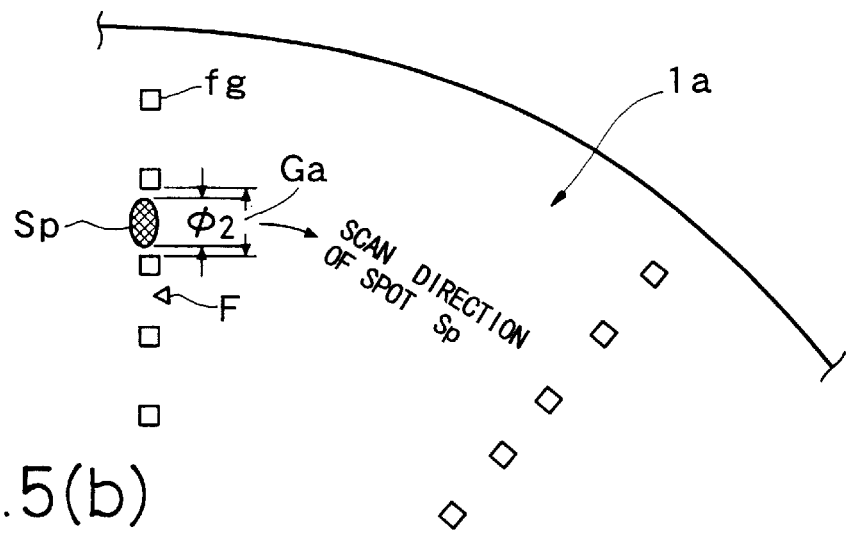
FIG. 5(a) shows a relation between a pitch of the false defects in a false defect row and a scanning laser spot and FIG. 5(b) shows a detection signal of the false defect.

The false defects fg within each false defect row FGR are arranged equidistantly with the same gap Ga which is slightly larger than the major axis length (width in the radial direction of the disk) φ2 of the laser spot Sp, as shown in FIG. 5(a).

The defect test is performed by mounting such reference disk 1a on the magnetic disk defect tester 11 shown in FIG. 1 or in lieu of the disk 1 of the magnetic disk defect tester 10 shown in FIG. 8 and the defect size is displayed on the display device 46 by using the detection value of false defect detected correspondingly to the level of the detection signal or the classification value of defects classified correspondingly to the level of the detection signal, so that the false defect rows of the reference disk 1a is displayed on the display 46 as a defect map. The defect map displayed depends upon the detection sensitivity regulation.

For example, when the detection sensitivity is set high, small size false defects are displayed as having the sizes thereof, while false defects whose sizes are larger than a certain size are displayed as having the same size since the size of false defects is changed in stepwise and the levels of detection signals thereof are saturated. On the contrary, when the detection sensitivity is set low, false defects having small sizes are not displayed since they are not detected, while false defects having large sizes are displayed as having the sizes thereof. According to the present invention, it is possible to regulate the detection sensitivity such that the optimal display is obtained by repeating the defect tests for the reference disk 1a a plurality of times while regulating the detection sensitivity through the control panel 47.

In this case, the regulation of the detection sensitivity of the tester is performed by regulating the voltage V applied to the light receiving element 322 (ADP), the gain and/or the threshold voltage E of the amplifier of the signal processing circuit 41 and/or the laser output of the laser light source 311, through the control panel 47. Further, the projection angle θT of the laser beam LT of the light projection system 31 and/or the light receiving angle θR of the light receiving system 32 may be regulated on demand.

For example, when the reference disk 1a having the 12 false defect rows is tested by the defect tester 11 to classify the sizes of the false defects with using a defect having one side length of 1 μm as the reference size, it is possible to regulate the various parameters through the control panel 47 such that the detection sensitivity becomes suitable to clearly display the respective false defect rows #1 to #12.

Further, when the reference disk 1a having the 24 false defect rows is tested by the defect tester 10 as mentioned previously, it is enough to regulate the detection sensitivity by regulating the various parameters of the tester such that 12 of the 24 false defect rows which are selected correspondingly to the measuring sizes for the defect size classification are clearly displayed. Further, a variation of the detection data for every test can be reduced by displaying 12 false defect rows having preliminarily determined sizes and regulating the detection sensitivity at a start of every test, and, thus, it is possible to restrict a variation of the detection data between different surface defect testers.

When the detection sensitivity is set definitely for only one size range in this manner, it is possible to regulate. the detection sensitivity through the control panel 47 such that the defect detection range corresponding to a size which is desired to be displayed on the image of detection result of the false defect rows of the calibration disk is clearly shown distinguishably from a display of other false defect rows. Therefore, it becomes possible to detect a specific size or a specific size range on preferential basis. Further, the regulation itself can be done simply while watching an image of the display screen, without skills. Therefore, the calibration of defect detection sensitivity while watching the detection result on the display screen can be done by any one whose skill is relatively low.

In order to perform a display using defect sizes of one of the false defect rows formed on the calibration disk as a reference, it is possible to provide in a position of the one false defect row a mark capable of displaying the latter false defect row.

In this embodiment, in order to recognize an arrangement of false defects even when the calibration disk itself includes a defect or defects, each false defect row includes at least three recesses or protrusions having substantially the same sizes and adjacent ones of these recesses or protrusions are arranged with a predetermined gap larger than the width of the laser spot in the radial direction.

That is, it is usually rare that a magnetic disk includes three or more real defects arranged in a row with a constant pitch. However, by arranging the false defects with predetermined pitch larger than the width of the laser spot Sp in the radial direction, it is possible to discretely detect the real defects. Further, even if another defect exists in between false defects in the form of recesses or protrusions, at least two of the false defects arranged in a radial row can be detected, so that the row can be recognized as a false defect row.

Figure 5B:
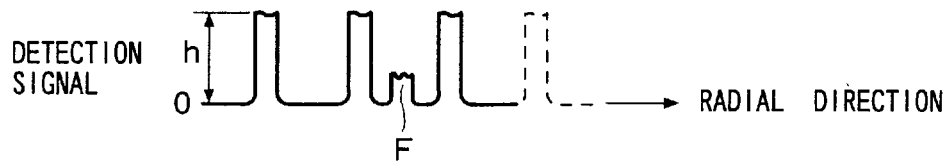

FIG. 5(b) illustrates a case where a defect detection signal of a reference disk 1a is detected in a radial direction by the signal processing circuit 41 by scanning the disk which is stationary with a laser spot Sp. Closely spaced 3 waveforms corresponding to 3 false defects fg appear on the defect detection signal. Therefore, it is possible to distinguish a waveform appearing on the detection signal which corresponds to a real defect F in the vicinity of the waveforms from the three waveforms corresponding to the false defects on the basis of a difference in amplitude between the waveform caused by the false defect and that caused by the real defect and a relation between these waveforms.

FIG. 4(c) shows another configuration of false defects in the false defect rows #1 to #12, which take in the form of protrusions fg'.

The size of false defect fg' is selected in the following range, where wg' is a diameter of the false defect and dg' is a height thereof:

Size of False Defect fg' wg': 0.5 μm, 1 μm, 3 μm, 5 μm, 10 μm, 20 μm dg: 0.025 μm, 0.05 μm, 0.2 μm, 0.75 μm, 0.01 μm

Figure 7:
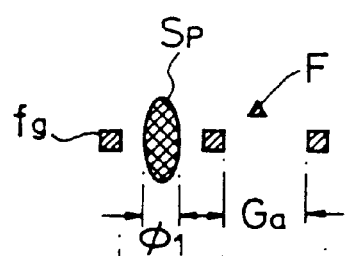
FIGS. 7(a) and 7(b) show a relation between a pitch of the false defects and a scanning laser spot and a detection signal of the false defect, respectively.
Figure 7:
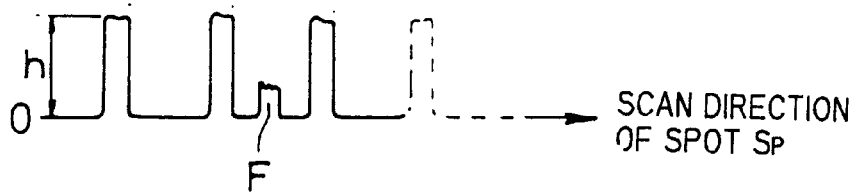
Figure 9:
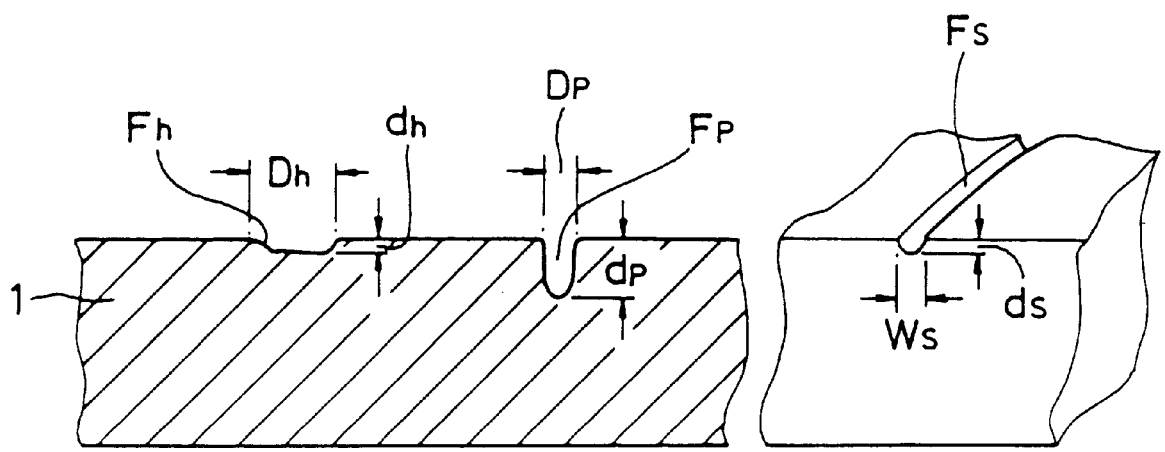
FIG. 9 illustrates various defects which may exist on a surface of a magnetic disk.

FIG. 6 shows a calibration disk 1b which a plurality of coaxially arranged arc rows of false defects fg in the form of square recesses are formed in every 60° sector of the calibration disk. The false defects fg in each row have the same size which is different from those in other rows. The depth of the false defects fg in each row increases successively in clockwise direction. Adjacent false defects fg are separated from each other by a distance Gb larger than a peripheral width ϕ1 of a laser spot Sp, as shown in FIG. 7(a). The depth of the respective false defects is selected from the previously mentioned dg or dg'.

The size of the false defects fg in the outermost row is largest and the size thereof is reduced gradually toward the innermost row. The size is selected from the previously mentioned wg or wg'. It is possible to reduce the number of false defects in one row by assigning a smaller size to false defects in an inner row next to the one row. A distance between the coaxial position of the one false defect row and the coaxial position of the inner row next to the one row is sufficiently larger than the radial width (major axis length) ϕ2 of the laser spot Sp. FIG. 7(b) corresponds to FIG. 5(b) and shows a detection signal of a false defects fg in the scanning direction of the laser spot Sp. Incidentally, radial dotted lines in FIG. 3 are mark lines provided on the calibration disk 1b for partitioning between the respective false defect rows and are formed by scratching with using a cutter, etc. Further, a reference position mark Mk can be provided similarly.

Figure 2:
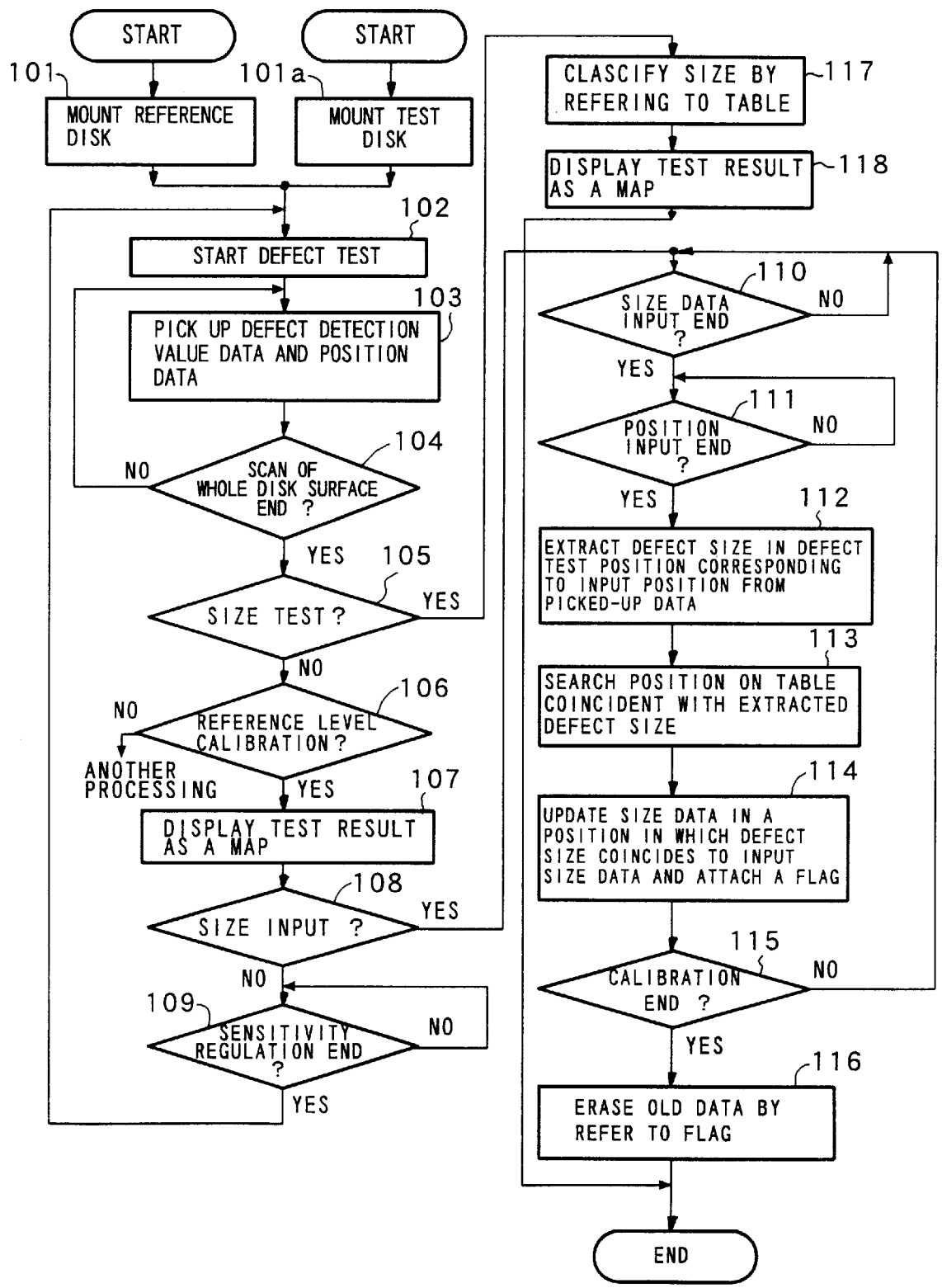
FIG. 2 is a flowchart of the defect test processing.

Now, the flow of the defect test processing will be described with reference to FIG. 2.

First, an operator mounts the reference disk 1a on the spindle 21 of the rotary mechanism 2 (step 101) and the MPU 42 calls the defect data acquiring program 43a in response to a predetermined key input of the start of test to execute the program. Upon this, the defect test is started (step 102). Then, the MPU 42 performs acquires the data of the detected defect value and the position data of the defect (step 103). Thereafter, the MPU 42 determines whether or not the scan of the whole surface of the disk 1 is completed (step 104). When the answer is NO, the operation is returned to the step 103.

The answer in the step 104 is YES and the scan of the whole surface of the disk 1 is completed, the MPU 42 determines whether or not the size test is performed (step 105). If NO, then it is determined whether the detection sensitivity calibration is performed (step 106), If YES in the step 106, the MPU 42 calls the defect test result map display program 43b and executes it to read out the data of the detected defect value and the position data, and the state of the reference disk 1a is map-displayed on the display (step 107). As mentioned previously, the detected defect value/ defect size table 43e at this time stores the conversion data with which the state of the reference disk 1a is displayed in the form similar to the actual form as the data value.

Thereafter, the MPU 42 determines whether or not there is a size input (step 108). If the answer in the step 108 is NO, the processing enters into a loop waiting the detection sensitivity regulation and it is determined whether or not the sensitivity regulation end key is input (step 109). The operator regulates the detection sensitivity through the control panel 47 and, when the sensitivity regulation end key is input, the processing of the MPU 42 is returned to the step 102 and the same test is repeated.

With this processing, the defect rows #1 to #12 of the reference disk 1a are caught clearly and, when the optimal regulation of sensitivity is performed, the answer in the step 108 becomes YES and the MPU 42 calls the determination reference data producing program 43c and executes it. And, then, the processing inters into the waiting loop waiting for the size data input from the input device 48 (step 110).

When the operator inputs the size from the input device 48, the MPU 42 waits for the position input by the mouse on the screen (step 111). When the position is input by pointing one of the defect rows #1 to #12 of the reference disk 1a corresponding to the size with the mouse on the screen of the display 46, the MPU 42 extracts the size of the defect in the defect detection position corresponding to the input position from the acquired size data (defect test result) (step 112), searches a position on the detected defect value/defect size table which coincides with the size of the extracted defect (step 113), updates the size data in the position on the table in which the defect size coincides by rewriting it to the input size data and attaches a flag in that position (step 114).

In this manner, a new pair of the detected defect value vs. the defect size is produced by rewriting the defect test result (picked-up data) to the defect size extracted correspondingly to the position assignment by means of the mouse. And, the MPU 42 determines whether or not the calibration is over (step 115). If NO, the processing is returned to the step 110.

By repeating the processing from the step 110 to the step 115, the size data of the false defect rows #1 to #12 or the false defect rows selected therefrom are rewritten sequentially in the detected defect value/defect size table 43e correspondingly to the levels of the actual output signals, so that the detected defect value/defect size table 43e contains data of the calibrated determination reference.

When the answer in the step 115 is YES, the MPU 42 erases the old data by referring to the update data (step 116). With this step, the calibration processing of the detection sensitivity is completed.

When the answer in the step 106 is NO, the processing is shifted to another processing.

When the operator mounts the test disk 1 on the spindle 21 of the rotary mechanism 2 (step 101a), the MPU 42 starts the defect test by calling and executing the defect data pick-up program 43a in the step 102. When the answer in the step 105 is YES, the MPU 42 calls and executes the defect size detection program 43d, classifies the sizes by referring to the updated detected defect value/defect size table 43e and counts the defects correspondingly to the sizes thereof (step 117). As a result, the calibrated size classified data corresponding to the level of the detection signal is obtained correspondingly to the defect detection value picked-up by the disk defect test.

Then, the MPU 42 calls and executes the defect test result map display program 43b, reads out the size data and the position data and displays the calibrated state of the test disk 1 on the display as a map (step 118). Of course, the count value of every defects may be also displayed on demand and the test result may be output to the printer 45.

It should be noted that, although the present invention has been described with respect to the data calibration on the defected defect value/defect size table, the present invention is not limited thereto. For example, it is possible to output the defect size data from a data conversion memory which outputs the defect size with using the signal level value as the address value. In such case, since data on this memory becomes the defect size data, it is enough to perform a rewrite for updating the data. Data which becomes the reference for determination of the defect size is not limited to such size data and threshold values corresponding to the sizes to be detected or threshold values corresponding to sizes to be classified may be set for the defect detection signal in the signal processing circuit 41 shown in FIG. 1 or 8.

The scanning of the disk with the laser spot Sp is not limited to the spiral scanning and it is enough to move the laser spot Sp relatively to the disk. Further, the light receiving element for receiving the scattered light from the defect may be CCD, etc.

Further, although the present invention has been described with using the mirror-polished disk of aluminum as the reference disk, a disk made of glass may be used as the reference disk. Further, the reference disk may be metal-plated. The reference disk is not limited to a magnetic disk or a substrate thereof and is applicable to any surface detect tester such as a wafer defect tester so long as it tests a surface defect of a circular work while rotating it.

What is claimed is:

1. In a surface defect tester which scans a surface of a disk to be tested with a laser spot while moving the laser spot relatively to said disk surface, receives a scattered light of the laser spot by a light receiving element thereof, obtains a detection signal by amplifying an output signal of said light receiving element and outputs, together with a position on the disk, a size of a defect corresponding to a level of the detection signal or a classified size classified correspondingly to the levels of the detection signals on said disk surface, a surface defect test method comprising the steps of:

performing a defect test for d calibration disk comprising n (n is an integer equal to or larger than 2) equiangularly spaced false defect rows each including 3 or more false defects formed radially or peripherally of said calibration disk, said false defects of each said false defect row being protrusions or recesses having substantially the same size, adjacent ones of said false defects of each said false defect row being physically separated by a predetermined distance larger than a width of a laser spot and the size of said false defects of a certain one of said false defect rows being different from that of said false defects of other said false defect rows;

regulating the detection sensitivity according to a result of the test;

producing data relating the level of the detection signal to the size of the false defect, from the result of test of the calibration disk as a reference data for size determination; and obtaining the defect size from the level of the detection signal when the defect test of the disk to be tested is performed on the basis of the reference data for determination.

2. A surface defect test method as claimed in claim 1, wherein the result of test is a detection value of the defect size corresponding to the level of the detection signal or a classification value of the defect size classified correspondingly to the level of the detection signal and is displayed on a display screen.

3. A surface defect test method as claimed in claim 2, wherein the stepwisely increasing or decreasing size of the false defect of the false defect rows is selected from a range of size of the defect to be detected and is an area of the false defect.

4. A surface defect test method as claimed in claim 2, wherein the stepwisely increasing or decreasing size of the false defect of the false defect rows is selected from a range of size of the defect to be detected and has the same area and different depth or height.

5. A surface defect test method as claimed in claim 2, wherein the stepwisely increasing or decreasing size of the false defect of the false defect rows is selected from a range of size of the defect to be detected and has different area and depth or different area and height.

6. A surface defect test method as claimed in claim 2, wherein a number of the false defects are provided along the radial directions and a mark indicative of a reference position is provided correspondingly to one of the n false defect rows.

7. A surface defect test method as claimed in claim 2, wherein said false defects have one of square shape, rectangular shape and circular shape and, when said false defects have the square or rectangular shape, one side length of said false defect is selected from a range from 0.5 $\mu$m to 20 $\mu$m and a depth or height thereof is selected from a range from 0.01 $\mu$m to 0.75 $\mu$m and, when said false defects have the circular shape, a diameter of said false defect is selected from a range from 0.5 $\mu$m to 20 $\mu$m and a depth or height thereof is selected from a range from 0.01 $\mu$m to 0.75 $\mu$m.

8. A surface defect test method as claimed in claim 1, wherein the reference data for determination is a threshold value corresponding to the size of the defect detected with respect to the level of the detection signal.

9. A surface defect test method as claimed in claim 1, wherein the disk to be detected is a wafer and the calibration disk is formed by forming the false defects on a sample wafer.

10. A surface defect tester for outputting, together with a position on a disk to be tested, a size of a defect corresponding to a level of a detection signal or a classified size classified correspondingly to the level of the detection signal on said disk by scanning a surface of said disk with a laser spot while moving the laser spot relatively to said surface of said disk, receiving a scattered light of the laser spot by a light receiving element thereof and obtaining the detection signal by amplifying an output signal of said light receiving element, said surface defect tester comprising:

a calibration disk comprising n (n is an integer equal to or larger than 2) equiangularly spaced false defect rows each including 3 or more false defects formed radially or peripherally of said calibration disk, said false defects of each said false defect row being protrusions or recesses having substantially the same size, adjacent ones of said false defects of each said false defect row being physically separated by a predetermined distance larger than a width of a laser spot and the size of said false defects of a certain one of said false defect rows being different from that of said false defects of other said false defect rows;

sensitivity regulation means for regulating the detection sensitivity;

reference data producing means for producing data relating the level of the detection signal to the size of the false defect, from the result of test of the calibration disk in a state in which the detection sensitivity of said surface defect tester is appropriately regulated by said sensitivity regulation means, as a reference data for size determination; and size detection means for obtaining the defect size from the level of the detection signal when the defect test of the disk to be tested is performed on the basis of the reference data for determination.

11. A surface defect tester as claimed in claim 10, further comprising a display and wherein the result of test is a detection value of the defect size corresponding to the level of the detection signal or a classification value of the defect size classified correspondingly to the level of the detection signal and is displayed on said display.

12. A surface defect tester as claimed in claim 11, further comprising input means for inputting the size of the defect and wherein a number of the false defects are provided along the radial directions, a mark indicative of a reference position is provided in one of said n false defect rows and said reference data producing means stores the size of the defect input by said input means in relation to the level of the selected detection signal.

13. A surface defect tester as claimed in claim 12, wherein said reference data producing means selects the level of the detection signal correspondingly to a display position on a screen displayed correspondingly to the result of test.

14. A surface defect tester as claimed in claim 11, wherein said false defects have one of square shape, rectangular shape and circular shape and, when said false defects have the square or rectangular shape, one side length of said false defect is selected from a range from 0.5 $\mu$m to 20 $\mu$m and a depth or height thereof is selected from a range from 0.01 $\mu$m to 0.75 $\mu$m and, when said false defects have the circular shape, a diameter of said false defect is selected from a range from 0.5 $\mu$m to 20 $\mu$m and a depth or height thereof is selected from a range from 0.01 $\mu$m to 0.75 $\mu$m.

15. A surface defect tester as claimed in claim 11, wherein the reference data for determination is a threshold value corresponding to the size of the defect detected with respect to the level of the detection signal.

* * * * *